(12) United States Patent
Foucaut et al.

(10) Patent No.: US 8,287,680 B2
(45) Date of Patent: Oct. 16, 2012

(54) MANUFACTURE OF BAGS FOR CONTAINING BIOLOGICAL SPECIMENS

(75) Inventors: Bertrand Marcel Alexandre Foucaut, Chevry (FR); Claude Fell, Nyon (CH)

(73) Assignee: Biosafe S.A., Eysins (CH)

(*) Notice: Subject to any disclaimer, the term of this patent is extended or adjusted under 35 U.S.C. 154(b) by 74 days.

(21) Appl. No.: 12/680,274

(22) PCT Filed: May 15, 2009

(86) PCT No.: PCT/IB2009/052032
§ 371 (c)(1),
(2), (4) Date: Mar. 26, 2010

(87) PCT Pub. No.: WO2009/138966
PCT Pub. Date: Nov. 19, 2009

(65) Prior Publication Data
US 2011/0259510 A1    Oct. 27, 2011

(30) Foreign Application Priority Data

May 16, 2008   (WO) .................. PCT/IB2008/051938

(51) Int. Cl.
*B29C 51/00*   (2006.01)
*B29C 65/70*   (2006.01)
(52) U.S. Cl. ........ 156/217; 156/292; 156/245; 264/248; 264/254

(58) Field of Classification Search .................. None
See application file for complete search history.

(56) References Cited

U.S. PATENT DOCUMENTS

| 3,123,509 | A | * | 3/1964 | Toegel | .................. 156/191 |
| 4,496,046 | A | | 1/1985 | Stone | |
| 5,928,214 | A | | 7/1999 | Rubinstein | |
| 6,146,124 | A | | 11/2000 | Coelho et al. | |
| 6,232,115 | B1 | | 5/2001 | Coelho et al. | |
| 6,361,642 | B1 | * | 3/2002 | Bellamy et al. | ............... 156/245 |
| 6,808,675 | B1 | | 10/2004 | Coelho et al. | |

FOREIGN PATENT DOCUMENTS

| GB | 2394690 | 5/2004 |
| JP | 1123727 | 5/1989 |

* cited by examiner

*Primary Examiner* — John L. Goff
*Assistant Examiner* — Barbara J. Musser
(74) *Attorney, Agent, or Firm* — Sturm & Fix LLP

(57) ABSTRACT

A method of manufacturing a bag (20) for the cryopreservation of thermolabile liquids. The manufacturing method is characterized by being versatile, simple and inexpensive and allows to manufacture single and multi-compartment bags without modifying the main sealing molds (31, 32). The relative size and the number of the compartments (28) can be modified without change in the molds. Only a closure sealing tool (50) must be adjusted as a function of the number of chosen compartments (28). The process is compatible with standard high frequency sealing processes. This method provides bags (20) with uniformly thick walls and with a predetermined bag volume.

12 Claims, 5 Drawing Sheets

MANUFACTURE OF BAGS FOR CONTAINING BIOLOGICAL SPECIMENS

FIELD OF THE INVENTION

The invention relates to a method for forming flexible bags, a system for manufacturing the bags and to the bag itself. More specifically, the invention relates to bags that contain blood substances or any biological or cellular substance. The invention in particular relates to a bag allowing cryogenic preservation while saving the internal bag substance from any cryogenic-preservation damaging effect.

BACKGROUND OF THE INVENTION

The preservation of blood and cellular biological thermolabile substances involves storage at very low temperatures. Thermolabile substances are substances that are easily altered or decomposed by heat. They can be contained in bags of plastics material; however, storage at very low temperatures creates stresses in the plastics materials and their joints and accordingly the bags used for this purpose must meet stringent requirements.

U.S. Pat. No. 5,928,214 described a bag of plastics material for containing biological liquid samples in particular for the cryopreservation of such samples, the bag being of the type made of facing plastics films joined around a sealed peripheral edge. The facing plastics films define a volume for containing a sample, in particular with several compartments communicating with one another by heat-sealable regions. This bag was described in connection with a system for concentrating white blood cells wherein the bag containing stem cells was divided into compartments limited by a heat seal that divided the stem cell freezing bag into two intimately attached but independent white cell containers with heat seals at the dividing locations. The larger main chamber keeps the bulk of the white cells and a smaller chamber is used for storage of a smaller fraction which can be separated from the main compartment without thawing.

U.S. Pat. Nos. 6,146,124; 6,232,115 and 6,808,675 describe respectively a mold, a bag useful for the cryopreservation of thermolabile substances and a method to manufacture the bag. The method uses a first mold having a portal-shaped recess and a recess with a planar surface having a radiused periphery circumscribing the planar surface and a peripheral ledge that circumscribes the radiused periphery. A sheet of plastics material is placed over the first mold and caused to conform to its shape. This formed sheet—which forms a half-shell of the bag—is then placed facing a similar formed sheet, or a flat sheet, and the two sheets are joined together by high frequency sealing around the periphery.

This manufacturing method is thus done in three different steps: individual pre-shaping of the two films with two different molds, one per film; positioning the two shaped films and the connector/tubes; and sealing of the bag borders with the connector and tubes This process allows manufacture of a bag with a 3-D shape therefore a reduced space for the storage. However, the process requires the aforementioned three steps, and if different bags with different compartments are to be produced, different two-part molds are needed.

Bags can also be formed by folding over a planar film and joining the peripheries by a seam.

The standard process for making flat plastic bags is by high-frequency welding around the periphery of two flat films. The tool is composed of two matrices which seal the borders of the film and the connector and tube sealing is included in the same step. This procedure is simple, however the bag keeps a 2-D shape and its storage capacity is limited. This therefore does not meet the specifications of certain types of bags which require a volume that fits in a specific protection cassette, for instance with 25 mL capacity for cryogenic storage. This simple process is thus inapplicable for bags which must have a given volume.

SUMMARY OF THE INVENTION

The invention relates to a simplified method of manufacturing a bag in particular for the cryopreservation of thermolabile liquids. The manufacturing method is versatile, simple and inexpensive and allows manufacture of single and multi-compartment bags without modifying the molds. Also, for any bag of given volume, the size of the bag's compartments and the number of these compartments can be modified without change in the main sealing molds. Moreover, the process can easily be adapted for making a large range of bags of different volume, for example from 10 ml to 500 ml. The method is compatible with standard high frequency sealing processes. This method provides bags with uniformly thick walls and with a predetermined bag volume. The invention results in bags with a substantially homogenous cross section so that the thickness of the bag containing any molecular substance is reduced which is very advantageous when several bags are placed together for storage.

According to a main aspect of the invention, there is provided a method of manufacturing a bag of plastics material for containing biological samples in particular for the cryopreservation of such samples, the bag being of the type made of facing spaced-apart layers of plastics film joined around a sealed peripheral edge whereby the facing spaced-apart plastics layers define a volume for containing a sample.

The inventive method comprises firstly placing between two superposed layers of a film of plastics material a molding insert having a shape, width and thickness that correspond to the inside shape, width and thickness of the bag to be formed. The layers are then formed into a part-formed bag whose inner shape, width and thickness are defined by the molding insert. The part-formed bag is made of spaced-apart layers that are closed around a portion of the bag periphery by joined edges, leaving open edges along one side that form an opening for removal of the molding insert. The joined edges of the part-formed bag are then sealed around a portion of the bag periphery, leaving the aforesaid opening in one side, the molding insert is removed from the part-formed bag through this opening, and the open edges of the spaced-apart layers of the part-formed bag are brought together along the opening. Lastly, the brought-together edges are sealed to form a bag that is closed around substantially its entire periphery by the sealed joined edges.

Preferably, the superposed layers are formed by folding over a film of plastics material. However, it is also possible to use two different films superposed one on the other.

The invention also proposes a mold for manufacturing a bag according to the above-defined as well as the mould in combination with a plurality of interchangeable closure sealing tools for forming the bag into one compartment or a plurality of compartments at choice.

The main sealing mold used to generate the overall natural shape of the bag is independent of the number of compartments, so it can stay the same for different configurations of the final bag (one or more compartments), only the sealing closure tool must change according to the desired number of compartments.

This new method can be used to produce bags of different final volume (for example, from 10 to 500 ml), but in this case the main molds must be adjusted for each different bag volume.

BRIEF DESCRIPTION OF THE DRAWINGS

The invention will be further described, by way of example, with reference to the accompanying drawings, in which.

DETAILED DESCRIPTION

The invention addresses the issues mentioned above. In order to store cryogenic preservation bags there is a need to realize a bag with a built-in volume shape. The invention consists in manufacturing such a bag with a simple and versatile process.

In general terms, the manufacturing process consists in positioning an insert 40 between one folded film 10',10" or two flat planar films for forming the bag walls (FIG. 1), before making a standard sealing by high frequency on three sides of the bags.

Figure 2:
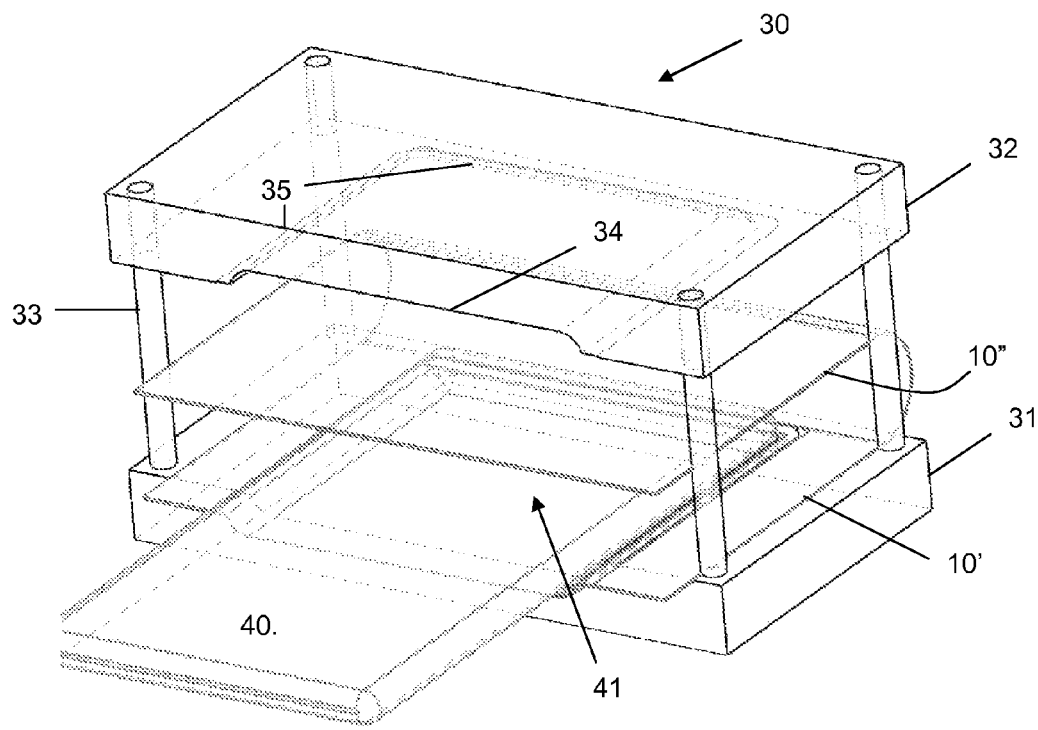
FIG. 2 is a corresponding perspective view of the molding assembly with a folded film inserted between the separated mold parts and with the molding insert being inserted.

Introduction of the insert 40 between a folded film 10',10" is shown in FIG. 2. The insert 40 generates a natural volume in the bag and so increases the nominal capacity at the same time.

Figure 3:
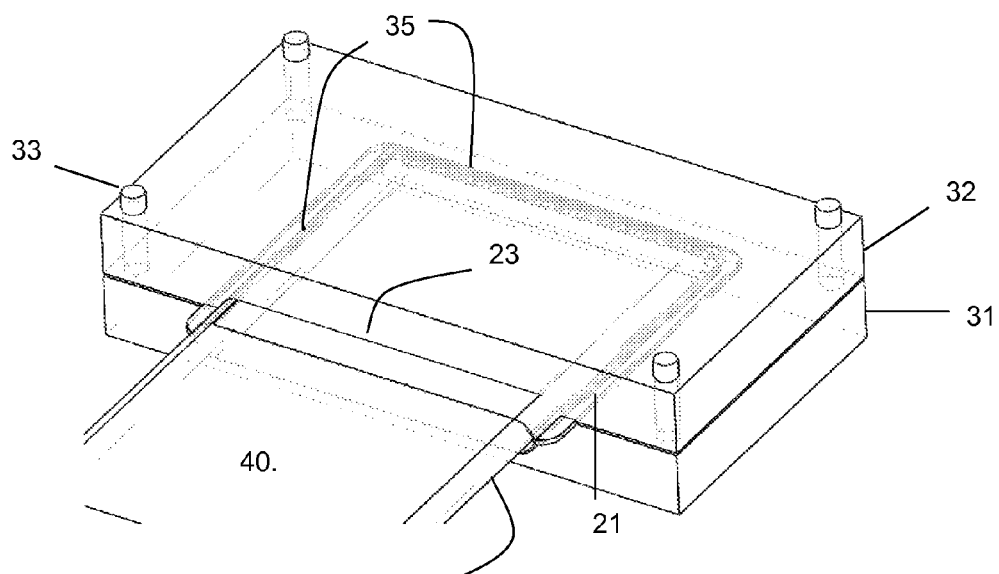
FIG. 3 shows the pressed-together mold parts for the sealing operation.

Then the two matrices 31,32 are closed around the film and the insert 40, as shown in FIG. 3. There is no film stretching during the forming process due to the fact that the film naturally follows the shape of the insert without mechanical strains. This results in a finished bag with uniformly thick walls, which is important for withstanding the low temperatures during cryogenic storage.

The insert 40 used during the sealing between the generally planar films 10',10" provides the bag's 3-D shape. This geometry provides space efficient storage for the finished and filled bags 20. The sealing process is then activated as illustrated in FIG. 3.

Figure 4:
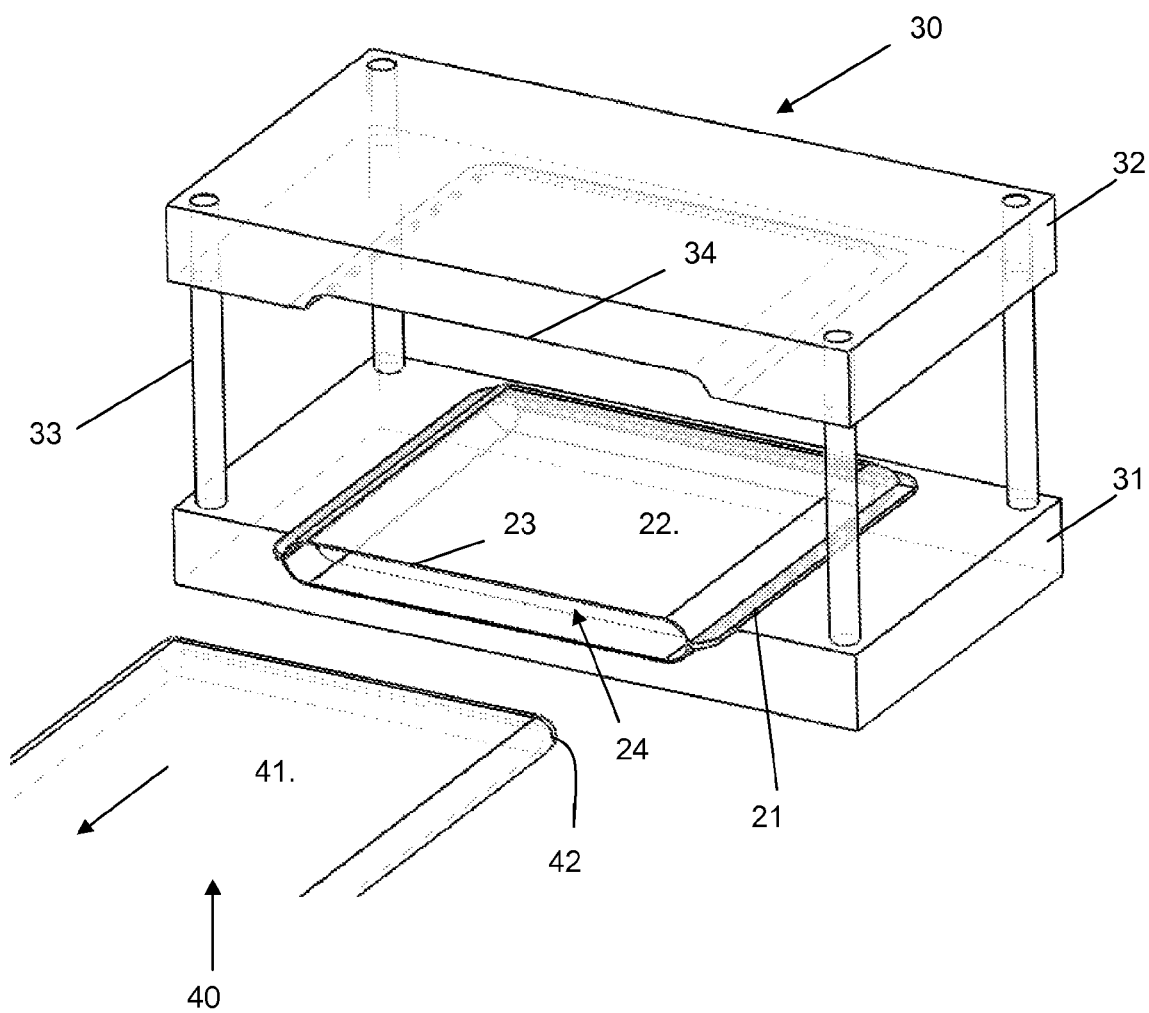
FIG. 4 is a perspective view of the molding assembly with the mold parts after separation, and with the molding insert in its outer removed position, the part-formed bag being shown resting in the lower mold part.

On FIG. 4 one can see that once the matrices are reopened we have a part-formed bag 22 with an inherent volume.

Figure 5:
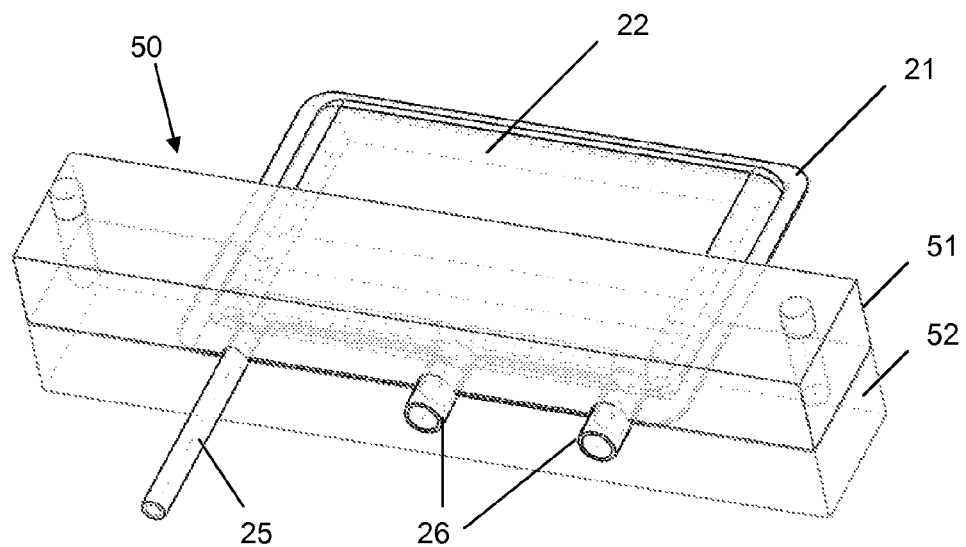
FIG. 5 shows a closure sealing tool forming the finished bag after insertion of a connector and tube in the open side and sealing this side.
Figure 6:
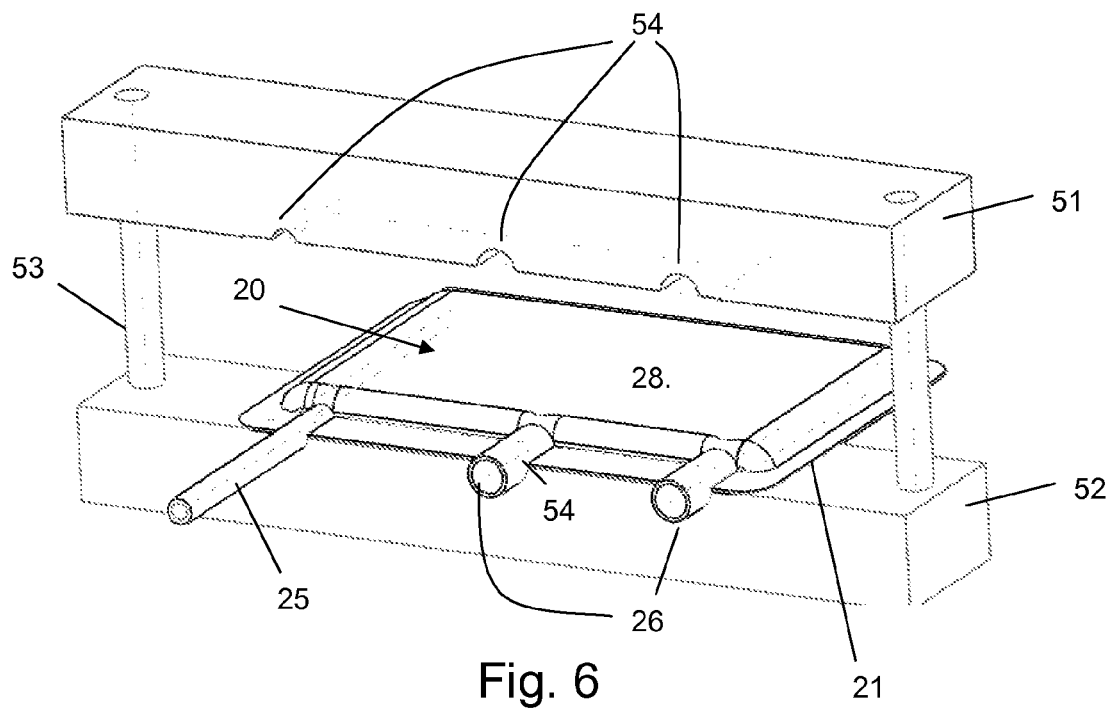
FIG. 6 shows the resulting one-compartment bag after opening of FIG. 5's closure sealing tool.

The second step is to insert the tubes 25 and connectors 26 and to seal the fourth side of the bag with a standard HF method, to form the bag 20 as illustrated in FIGS. 5 and 6.

This solves the space and storage problem described above as the thickness of the bag 20 will remain constant, reducing thus the thickness of the bag and saving precious storage place.

The manufacturing process is simplified by comparison to the prior art. In order to create a built-in volume and 3-D shape in the bag, the process uses 1 or 2 generally planar films positioned on each side of an insert 40 having the appropriate length, width and thickness. Then standard HF sealing methods is used to seal three sides of the bag.

In particular, the inventive method can for example be implemented by the following series of steps.

Figure 1:
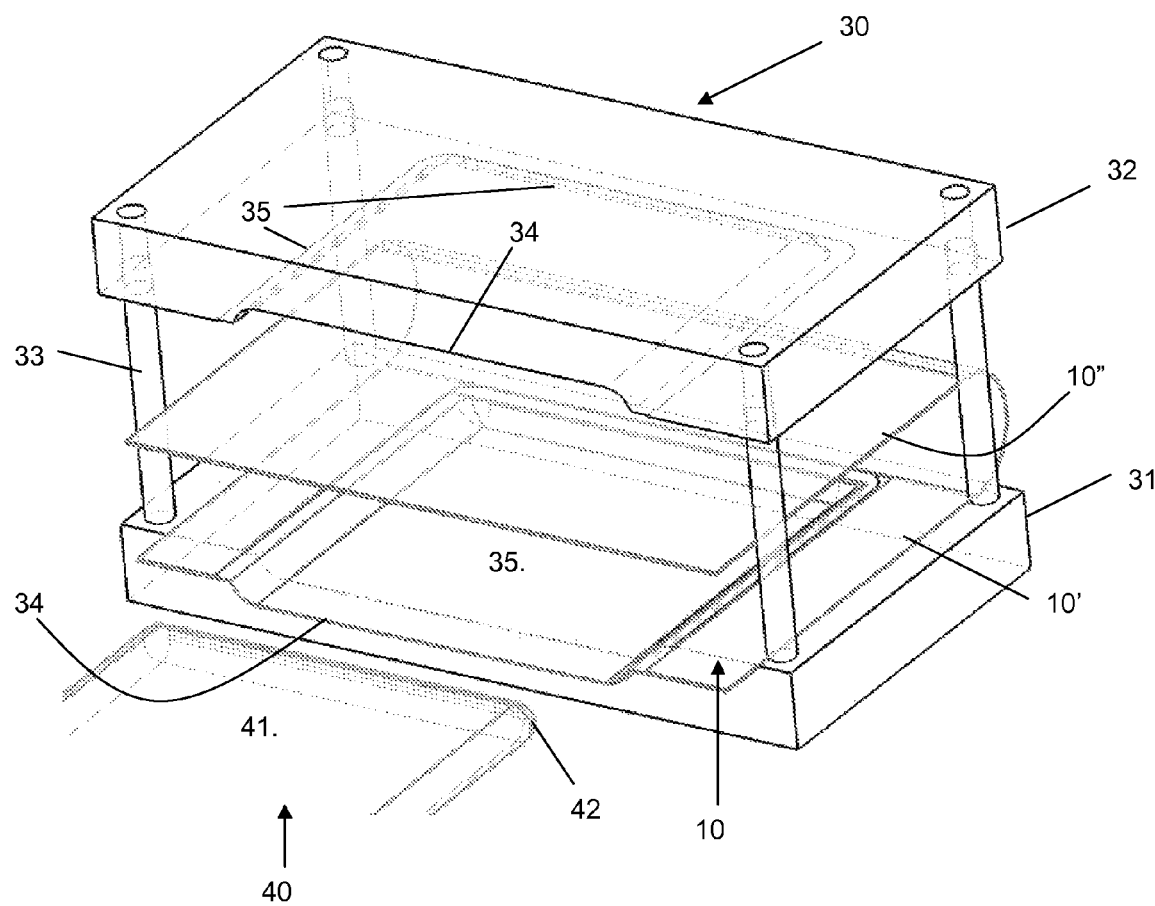
FIG. 1 is a perspective view of a molding assembly with a folded film inserted between separated mold parts and with a molding insert in an outer position.

Two superposed layers 10',10" formed by folding over a film 10 of plastics material are positioned between the spaced-apart lower part 31 and upper part 32 of a main sealing mould 30, as shown in FIG. 1. A molding insert 40 that has a shape, width and thickness that corresponds to the inside shape, width and thickness of the bag to be formed is placed between the layers 10',10" in the main sealing mould 30, as shown in FIG. 2. On its insertable end section 41 that fits in the cavity 35 of the main sealing mold 30, the insert 40 has rounded edges 42 corresponding to the rounded shape of the bag's edges.

This cavity 34 in the main sealing mold 30 corresponds to the outside shape and dimensions of the bag 20 to be manufactured. Cavity 34 is closed around a portion of its periphery, namely around three sides, corresponding to a portion of the periphery of the bag to be manufactured. This cavity 34 has an opening 35 that opens into a lateral face of the two mold parts 31,32.

The molding insert 40 has an inserted position in which the insertable end section 41 is situated in the cavity 34 between the two mold parts 31,32 when they are placed together. This end section 41 of the molding insert has a shape and thickness that corresponds to the inside shape and thickness of the bag 20 to be formed in the cavity 34 and is insertable into and removable laterally from the cavity 34 via the opening 35 by inserting or removing the insert 40 when the two mold parts 31,32 are placed together or spaced apart.

The mould parts 31,32 are positioned using standard mechanical alignment methods schematically illustrated by way of example as columns 33 by which they are slidably mounted together. By bringing together the two mould parts as shown in FIG. 3, the layers 10',10" are formed into a part-formed bag 22 whose inner shape, width and thickness are defined by the molding insert 40. The part-formed bag 22 (see FIG. 4) is made of spaced-apart layers of the plastics film that are closed around three edges of the bag periphery by joined edges 21, leaving open edges 23 along one side that form an opening 24 for removal of the molding insert 40. The joined edges 21 of the part-formed bag 22 around the three edges of the bag periphery are sealed using high-frequency sealing between the two mould parts 31,32, leaving the opening 24 in one side, that will be sealed in the subsequent operation. As can be seem in FIG. 3 the open edges that will be sealed in the subsequent operation protrude from the side of the closed sealing mold 30.

The molding insert 40 is removed from the part-formed bag 22 through opening 24, as shown in FIG. 4.

The part-formed bag 22 is then inserted in a closure sealing tool 50, FIG. 5, which in this example is adapted for forming a one-compartment bag. The closure sealing tool 50 has a lower tool part 51 and an upper tool part 52 with facing corresponding recesses 54 for receiving tubes 25, portals 26 or any other connectors that are inserted in the previously-described opening 24 in the part-formed bag 22.

The lower and upper parts 51,52 of the closure sealing tool are as before positioned using standard mechanical alignment methods schematically illustrated by way of example as columns 33 by which they are slidably mounted together. This allows the two parts to be brought together, as shown in FIG. 5 in order to bring together the open edges of the spaced-apart layers of the part-formed bag 22 along the opening 24. The brought-together edges are then sealed by high-frequency sealing to form a bag that is closed around substantially its entire periphery by the sealed joined edges 21, leaving apertures at the locations of the tubes/portals or connectors 25/26. In this example, the peripheral sealed edge 21 surrounds and defines a single internal compartment 28.

Figure 7:
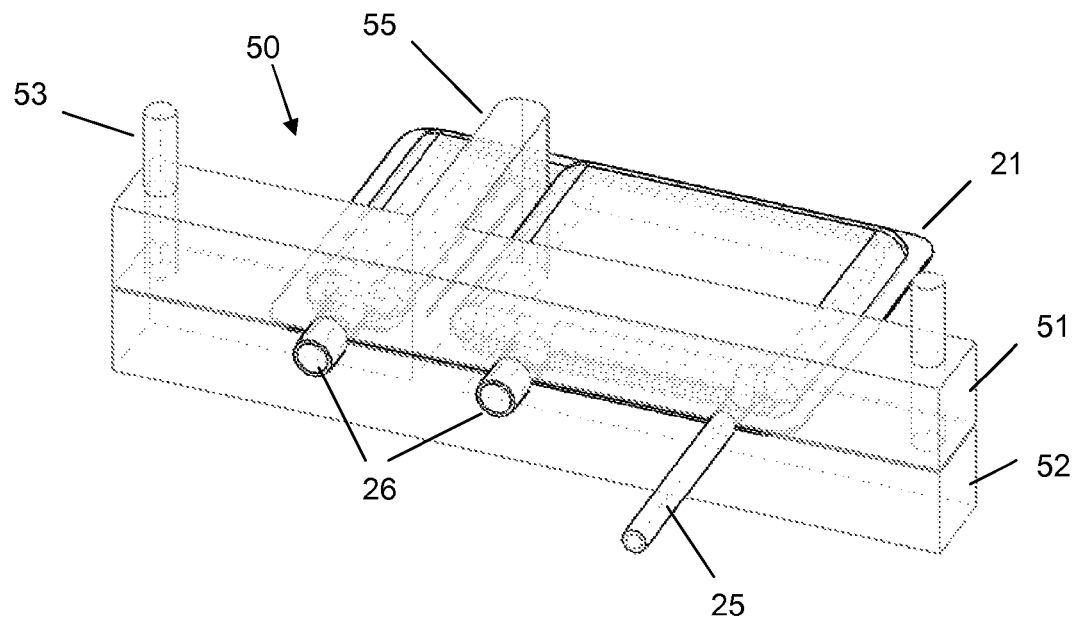
FIG. 7 shows another closure sealing tool for forming a two-compartment bag after insertion of a connector and tube in the open side and sealing this side.
Figure 8:
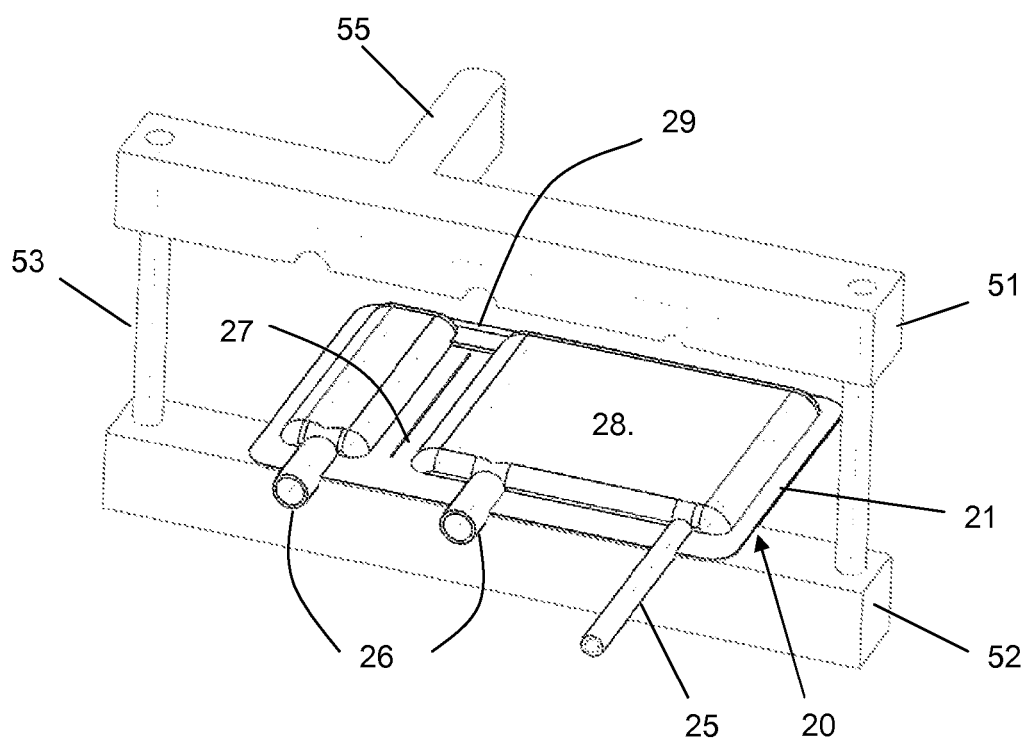
FIG. 8 shows the resulting two-compartment bag after opening of FIG. 7's closure sealing tool.

FIGS. 7 and 8 show a special sealing closure tool 50 for forming the bag 20 with a sealed area 27 whereby the bag 20 is divided into two (or more) compartments 28 that communicate with one another at 29 adjacent the edge of the bag opposite said brought-together edges along the opening 24. For this purpose, the upper tool part 51 has a projection 55 at the location for forming the sealed area 27. This projection 55 presses together the plastics layers at the location of the sealed area 27 when the tool parts 51,52 are brought together. High-frequency sealing is then made along the joined edges at the location of the opening 24, and along the projection 55

In this way, the bag of given size and shape produced using the main sealing mold 30 can have one or and desired number of compartments 28 and the relative sizes of the compartments can be varied at will without any need to change the main sealing mold 30, making the process very versatile.

The invention also contemplates filling the bag 20 with a sample through an aperture (25,26), whereupon the aperture is sealed and the sample in the bag is frozen. In particular, the finished bag 20 can be filled with a biological sample followed by sealing the compartments 28 of multi-compartment bags from one another by sealing together the facing parts 29 of the films where the compartments communicate.

Usually, as described, the bags 20 are of overall generally rectangular shape, and the first sealing step takes place by sealing together the joined edges of the part-formed bag 22 along three sides of the rectangular bag, the opening 24 in the part-formed bag being located usually along a long side of the rectangular bag where the apertures for tubes 25 and connectors 26 are located.

The invention claimed is:

1. A method of manufacturing a bag (20) of plastics material for containing biological samples in particular for the cryopreservation of such samples, the bag being of the type made of facing spaced-apart layers (10',10") of a plastics film joined around a sealed peripheral edge (21) whereby the facing spaced-apart layers of plastics film define a volume for containing a sample, the method comprising:
    (a) placing between two superposed layers (10', 10") of a film of plastics material a molding insert (40) having a shape, width and thickness that corresponds to the inside shape, width and thickness of the bag to be formed,
    (b) forming the layers into a part-formed bag (22) whose inner shape, width and thickness are defined by the molding insert (40), the part-formed bag being made of spaced-apart layers that are closed around a portion of the bag periphery by joined edges, leaving open edges (23) along one side that form an opening (24) for removal of the molding insert (40);
    (c) sealing together said joined edges (23) of the part-formed bag (22) around a portion of the bag periphery, leaving said opening (24) in one side;
    (d) removing the molding insert (40) from the part-formed bag (22) through said opening (24);
    (e) bringing together the open edges (23) of the spaced-apart layers of the part-formed bag (22) along said opening (24); and
    (f) sealing the brought-together edges to form a bag (20) that is closed around substantially its entire periphery by the sealed joined edges (21), characterized in that said method comprises using a mold (30) that comprises:
    two mold parts (31,32) that can be spaced apart and brought together in facing relationship, the two mold parts defining therebetween when they are placed together a cavity (34) that corresponds to the outside shape and dimensions of the bag (20) to be manufactured, this cavity (34) being closed around a portion of its periphery corresponding to a portion of the periphery of the bag to be manufactured and having an opening (35) that opens into a lateral face of the two mold parts (31,32); and
    the molding insert (40) has an inserted position in which an insertable end section (41) of the insert is situated in the cavity (34) between the two mold parts when they are placed together, this end section (41) of the molding insert having a shape and thickness that corresponds to the inside shape and thickness of the bag (20) to be formed in the cavity and being insertable into and removable laterally from the cavity (34) via said opening (35) by inserting or removing the insert (40) when the two mold parts (31,32) are placed together or spaced apart.

2. The method of claim 1, further comprising inserting at least one portal (26) or tube (25) between the spaced-apart layers before sealing, to form a bag (20) with at least one portal (26) or tube (25) forming an aperture in one edge of the bag.

3. The method of claim 2, wherein the portal(s) (26) and/or tube(s) (25) are inserted between the spaced-apart layers along said opening (24) after the molding insert (40) has been removed in step (d) and before said open edges (23) are brought together and sealed in steps (e) and (f).

4. The method of claim 1, wherein steps (e) and (f) are performed to form the bag with a peripheral sealed edge (21) defining a single internal compartment (28).

5. The method of claim 1, wherein during steps (e) and (f) a sealed area (27) is formed dividing the bag into two or more internal compartments (28) that communicate with one another adjacent the edge of the bag (20) opposite said brought-together edges (23).

6. The method of claim 5, which further comprises filling the bag (20) with a sample and sealing the compartments (28) from one another by sealing together the facing parts (29) of the films where the compartments communicate.

7. The method of claim 1, wherein the bags (20) are of overall generally rectangular shape, and step (c) takes place by sealing together the joined edges of the part-formed bag along three sides of the generally rectangular bag.

8. The method of claim 7, wherein said opening is along a long side of the generally rectangular bag (20).

9. The method of claim 1, wherein the edges of the bag (20) are sealed by high-frequency sealing.

10. The method of claim 1, wherein the bag (20) is filled with a sample through an aperture (25, 26), the aperture is sealed and the sample in the bag is frozen.

11. The method of claim 1, comprising:
    (a) placing between the two spaced apart mold parts (31, 32) the two superposed layers (10',10") of the film of plastics material with the molding insert (40) located between the two layers and with the insert's end section (41) positioned in registry with said cavity (34) in the two mold parts (31,32);

(b) bringing the two mold parts (31,32) together with the molding insert (40) placed in its inserted position in the cavity (34), to form the film into the part-formed bag (22) whose outer thickness is delimited by the dimensions of the cavity (34) that surrounds the inserted end section (41) of the molding insert;

(c) sealing these joined edges of the part-formed bag;

(d1) separating the two mold parts (31,32); and (d2) removing the molding insert (40) from its inserted position and from its engagement in the part-formed bag (22).

12. The method of claim 1 wherein steps (e) and (f) are performed to close and seal the joined edges and to form the bag (20) into one compartment or a plurality of compartments (28) by using an appropriate closure sealing tool (50).

* * * * *